United States Patent
Taylor (10) Patent No.: US 8,246,350 B2
(45) Date of Patent: Aug. 21, 2012

(54) SAFETY ATTACHMENT FOR ORTHODONTIC WIRES AND PLIERS TO APPLY ATTACHMENT

(76) Inventor: Helen Taylor, Catbrook (GB)

( * ) Notice: Subject to any disclaimer, the term of this patent is extended or adjusted under 35 U.S.C. 154(b) by 202 days.

(21) Appl. No.: 12/521,383

(22) PCT Filed: Jan. 4, 2008

(86) PCT No.: PCT/GB2008/000018
§ 371 (c)(1),
(2), (4) Date: Jun. 26, 2009

(87) PCT Pub. No.: WO2008/084198
PCT Pub. Date: Jul. 17, 2008

(65) Prior Publication Data
US 2010/0323316 A1 Dec. 23, 2010

(30) Foreign Application Priority Data

Jan. 11, 2007 (GB) .................................. 0700495.5
Jan. 4, 2008 (WO) ................. PCT/GB2008000018

(51) Int. Cl.
*A61C 3/00* (2006.01)
(52) U.S. Cl. ............................................. 433/22; 433/4
(58) Field of Classification Search .............. 433/4, 144, 433/163, 229, 11–22; 30/1.5; 43/43.12–44.95, 43/49; 140/93 D, 106, 121; 111/49; 191/44.1; 81/300; 606/210; 294/99.2
See application file for complete search history.

(56) References Cited

U.S. PATENT DOCUMENTS

| | | | | | |
|---|---|---|---|---|---|
| 1,464,807 A | * | 8/1923 | Clark | ............................. | 433/144 |
| 1,898,212 A | * | 2/1933 | Polcini | ............................. | 24/128 |
| 2,765,686 A | * | 10/1956 | Deline | ........................ | 72/409.04 |
| 2,904,924 A | * | 9/1959 | Tashiro | .......................... | 43/44.89 |
| 3,084,469 A | * | 4/1963 | Stratton | ........................ | 43/43.14 |
| 3,581,400 A | * | 6/1971 | Snead | ................................ | 433/4 |
| 3,597,823 A | * | 8/1971 | Nelson | ....................... | 72/409.01 |
| 3,914,976 A | * | 10/1975 | Karr | ................................. | 72/339 |
| 4,348,808 A | * | 9/1982 | Nalbandyan | .................... | 30/134 |
| 4,395,824 A | * | 8/1983 | Puro | ............................... | 30/134 |
| 4,639,219 A | * | 1/1987 | Gagin | ............................. | 433/22 |
| 4,682,598 A | * | 7/1987 | Beraha | .......................... | 606/142 |

(Continued)

FOREIGN PATENT DOCUMENTS
DE 3149544 C1 7/1983

*Primary Examiner* — Cris L Rodriguez
*Assistant Examiner* — Matthew Saunders
(74) *Attorney, Agent, or Firm* — Goodman Allen & Filetti PLLC (57) ABSTRACT

A safety attachment for application to orthodontic wire in the mouth of a patient comprises a safe-end portion to be crimped onto the orthodontic wire, which once in place on the wire has no sharp edges. The safety attachment comprises upper and lower portions secured to each other by a hinge. One or both of the inner surfaces of the attachment may be textured to improve grip on the wire. The safety attachment may include means for retention by application pliers. Pliers designed for application of a safety attachment have upper and lower beaks, wherein the upper beak includes means to crimp the safe-end portion onto an orthodontic wire and the lower beak includes means to retain the safety attachment prior to applying the safe-end portion to the wire and after application release the safe-end portion leaving it in place on the wire in the patient's mouth.

20 Claims, 9 Drawing Sheets

U.S. PATENT DOCUMENTS

| | | | | |
|---|---|---|---|---|
| 4,716,886 A | * | 1/1988 | Schulman et al. | 606/120 |
| 4,797,094 A | * | 1/1989 | Karwoski | 433/22 |
| 4,807,622 A | * | 2/1989 | Ohkaka et al. | 606/167 |
| 4,817,602 A | * | 4/1989 | Beraha | 606/137 |
| 5,037,296 A | * | 8/1991 | Karwoski | 433/8 |
| 5,084,935 A | * | 2/1992 | Kalthoff | 7/132 |
| 5,306,142 A | * | 4/1994 | Richards | 433/22 |
| 5,344,315 A | * | 9/1994 | Hanson | 433/20 |
| 5,766,005 A | * | 6/1998 | Casey | 433/15 |
| 5,910,008 A | | 6/1999 | Tran | |
| 6,015,417 A | * | 1/2000 | Reynolds, Jr. | 606/151 |
| 6,996,931 B1 | * | 2/2006 | Ratte | 43/44.91 |
| 7,182,595 B2 | * | 2/2007 | Smith et al. | 433/4 |
| 7,713,057 B2 | * | 5/2010 | de Salazar Vinas | 433/17 |
| 2002/0076672 A1 | | 6/2002 | Enoch et al. | |
| 2007/0042314 A1 | * | 2/2007 | Brosius | 433/22 |
| 2007/0218417 A1 | * | 9/2007 | de Salazar Vinas | 433/17 |
| 2009/0013585 A1 | * | 1/2009 | Acworth et al. | 43/44.89 |

* cited by examiner

SAFETY ATTACHMENT FOR ORTHODONTIC WIRES AND PLIERS TO APPLY ATTACHMENT

CROSS-REFERENCE TO RELATED APPLICATIONS

This application is a continuation of International Application No. PCT/GB2008/000018, filed Jan. 4, 2008, which claims priority from GB Patent Application No. 0700495.5, filed Jan. 11, 2007. The disclosures of both applications are incorporated herein by reference.

BACKGROUND OF THE INVENTION

The invention relates to a safety attachment for orthodontic wires and pliers to apply the safety attachment.

Orthodontic braces consist of brackets that are affixed to teeth, and orthodontic wires, which will simply be referred to hereinafter as wires for the sake of brevity that attach to those brackets to deliver a controlled force to move and guide the teeth, such that they come into the desired alignment. At the beginning of treatment, the wires used are of small diameter, as small as 0.3 mm or less, and are very flexible. As treatment progresses the wires used may be of larger diameter and thus be less flexible.

Using the small diameter wires at the start of treatment in particular poses three problems, as follows.
1. The flexibility of the wires allows them to distort and pull out of the bracket on the last tooth in the dental arch usually a molar, with a tube type of orthodontic bracket.
2. When placing the wires, excess wire is clipped off from behind the last most tooth. Pliers designed to cut and hold the excised wire fragment, so that the fragment can safely be removed from the mouth, can fail to adequately hold very thin wires such that the fragment of wire is dropped in the back of the patient's mouth and it is then difficult to locate and recover.
3. As teeth align during the orthodontic treatment, less length of wire is needed and excess wire protrudes at the back behind the last most tooth. This can occur between appointments with the orthodontist and can cause ulceration to the cheeks of the patient, even if the end of the wire is curved into a loop. In addition, it is difficult to access the wire at the back of the mouth in order to adequately turn it into a loop. Furthermore, modern flexible-alloy wires resist deformation and do not readily accept the imposition of a shape-change, making it difficult to obtain adequate curvature to create a loop that makes the wire safe.

All three problems pose a health risk to orthodontic patients and generate emergency visits, which increase the workload of the orthodontist. A solution to these problems is therefore highly desirable.

It is an object of the present invention to provide a safety attachment for orthodontic wires and pliers to apply the attachment, which mitigate the above described problems.

SUMMARY OF THE INVENTION

According to a first aspect of the present invention there is provided a safety attachment specifically designed for application to orthodontic wire in the mouth of a patient, the safety attachment comprising a safe-end portion to be crimped onto the orthodontic wire, which once in place on the wire has no sharp edges characterized in that it comprises upper and lower portions secured to each other by a hinge.

Further features of the safety attachment are set out in the accompanying claims.

According to a second aspect of the invention there are provided pliers specifically designed for application of a safety attachment according to the first aspect of the invention, the pliers having upper and lower beaks, wherein the upper beak includes means to crimp the safe-end onto an orthodontic wire and the lower beak includes means to retain the safety attachment prior to applying the safe-end to the wire and after application release the safe-end leaving it in place on the wire in the patient's mouth.

Further features of the pliers are set out in the accompanying claims.

BRIEF DESCRIPTION OF THE DRAWINGS

Embodiments of the safety attachment and the pliers will now be described, by way of example only, with reference to the accompanying Figures in which.

DETAILED DESCRIPTION OF THE PREFERRED EMBODIMENT

Figure 1A:
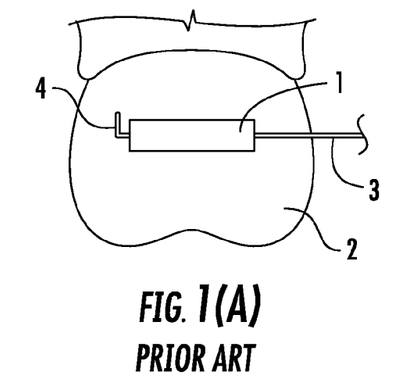
FIG. 1(a) schematically illustrates a side view of the prior art problem to be solved.
Figure 1B:
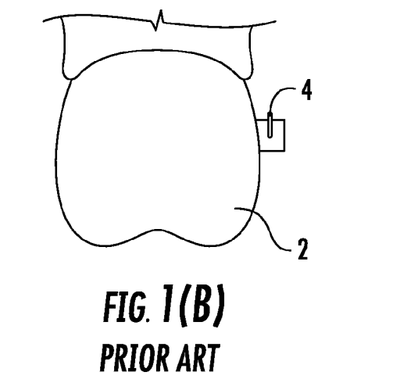
FIG. 1(b) schematically illustrates a back view of the prior art problem to be solved.

Referring first to FIGS. 1(a) and 1(b) an orthodontic fixed appliance includes a bracket, called a tube 1 that is affixed to a molar tooth 2. Through this tube 1 passes a wire 3, the protruding portion of which, in the prior art, is then bent at an angle to create a turned end 4 as it emerges from the tube behind the molar tooth. The bending of the wire 3 to create the turned end 4 is designed to do two things. The first is to help prevent the wire 3 from being pulled back forwards through the tube 1 accidentally. The second is that it presents a curved profile of wire 3 rather than a cut and sharp end, which might cause trauma to the cheeks of the patient. However, creating an adequate angle to achieve a satisfactory result, especially in small diameter flexible-alloy wires, is difficult.

Often the wire 3 still pulls through the tube 1 and sometimes the turned end 4 unbends between appointments so that a sharp end is produced.

Figure 2A:
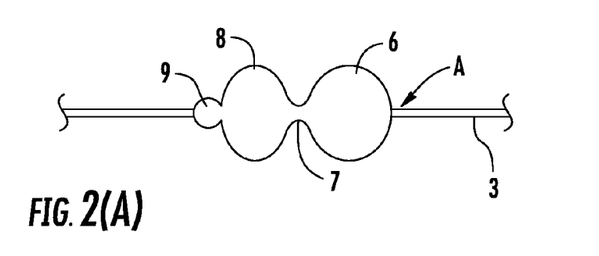
FIG. 2(a) schematically illustrates a top view of a first embodiment of a safety attachment according to the invention.
Figure 2B:
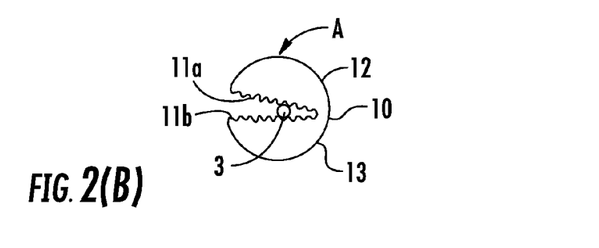
FIG. 2(b) schematically illustrates an end view of the first embodiment of the safety attachment of FIG. 2(a)
Figure 2C:
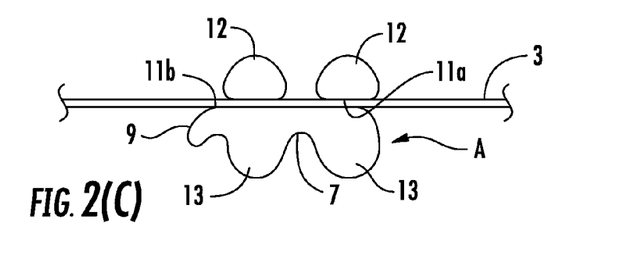
FIG. 2(c) schematically illustrates a side view of the first embodiment of the safety attachment of FIG. 2(a)

Referring now to FIGS. 2(a) through 2(c), a first embodiment of the invention will be described. In its initial form a safety attachment A consists of four portions: a first portion is a safe-end portion 6, which in use is closed around the wire 3 and is left on the wire 3 in the patient's mouth as a safe-end; a second portion comprises a connecting isthmus 7; a third portion is a wire-retaining portion 8, which in use is closed around the excised wire fragment, maintaining hold of it so that it can be removed with the pliers, and a fourth portion is a retaining lug 9, that is retained in the jaws of pliers as will become clear so that the excised fragment can be safely removed from the patient's mouth without danger of being dropped.

When viewed from the end as in FIG. 2(b), the safety attachment A resembles a split-shot weight as used in angling, with upper and lower, portions 12 and 13 that are connected on one side only by a thin area of metal which acts as a hinge 10. The internal faces 11a, 11b of the upper and lower portions 12 and 13 are serrated to increase grip on the wire 3. When viewed from the side as in FIG. 2(c), the division between the upper portion 12 and the lower portion 13 can be seen. The retaining lug 9 and connecting isthmus 7 are positioned level with the upper face 11b of the lower portion 13.

Figure 3A:
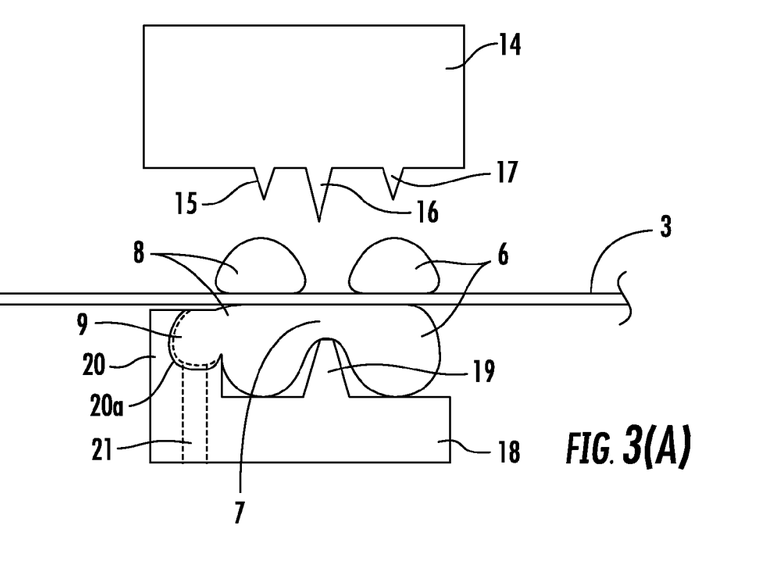
FIG. 3(a) schematically illustrates side view of beaks of pliers used to apply the first embodiment of the safety attachment of FIG. 2.
Figure 3B:
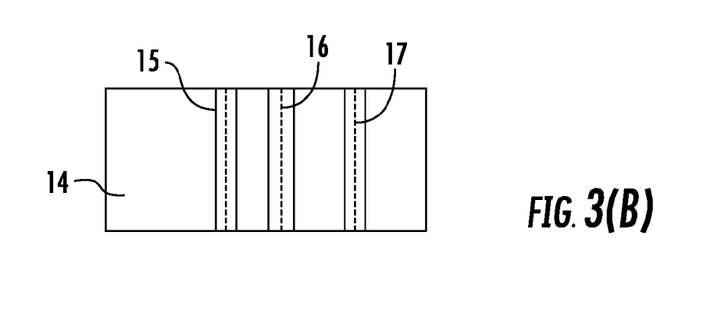
FIG. 3(b) schematically illustrates the lower face of the upper beak of the pliers of FIG. 3(a)
Figure 3C:
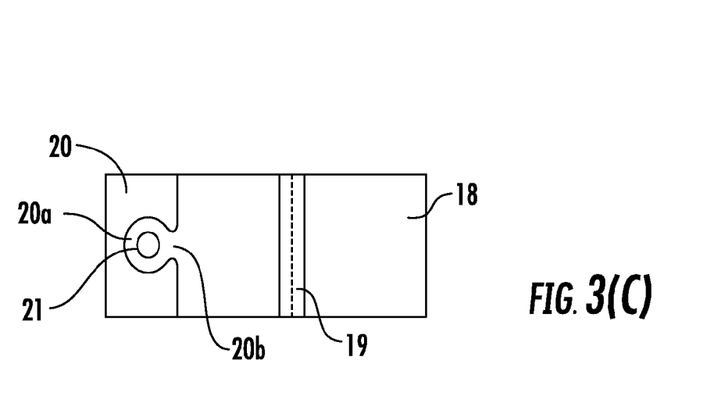
FIG. 3(c) schematically illustrates the upper face of the lower beak of the pliers of the pliers of FIG. 3(a)

Referring now to FIGS. 3(a) through 3(c), the safety attachment A is applied to the wire 3 using specially designed pliers the upper beak 14 and lower beak 18 of which are shown schematically. The beaks 14, 18 are formed integrally with or secured to arms (not shown) of pliers in conventional manner to provide the entire tool. The upper beak 14 carries three blades 15, 16 and 17. The first blade 15 is to crimp the wire-retaining portion 8 so that it grips the wire 3. The second blade 16 is to cut through the connecting isthmus 7. The third blade 17 is to crimp the safe-end portion 6 so that it grips the wire 3. The lower beak 18 carries one blade 19 to fit under the connecting isthmus 7 and which is aligned with the second blade 16 of the upper beak 14, this ensures that when the pliers are closed there is a clean cut of both the isthmus 7 and the wire 3. The crimping blades 15 and 17 may be multiple blades and/or broad flat ended blades in order to provide the best crimping action without risk of cutting through the portions 6 and 8 of the safety attachment A.

The lower beak 18 also includes an upstand 20 within which is provided a recess 20a, with an opening 20b facing the blade 19. The recess 20a is shaped for receipt of the retaining lug 9. The lug 9 and recess 20a cooperate to prevent the safety attachment A being accidentally dislodged during use in the patient's mouth, and to ensure that the wire retaining portion 8 and wire fragment are safely removed from the patient's mouth.

A bore 21 runs vertically through the upstand 20 from the outer face of the lower beak 18 and the recess 20a. The bore 21 is provided to allow insertion of a dental probe or similar instrument to remove the lug 9 and retained wire fragment following attachment of the safe-end 6 to the wire 3 in the patient's mouth. The lug 9 and retained wire fragment can thus be dropped directly into a secure sharps container in accordance with health and safety procedures.

Figure 4A:
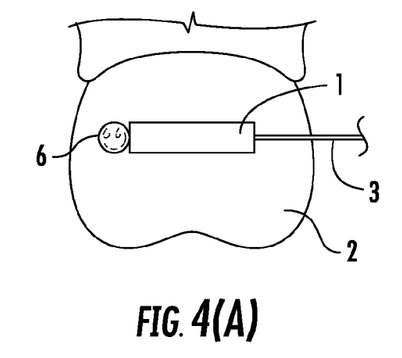
FIG. 4(a) schematically illustrates a side view of the attachment according to the invention in place on the wire after application using the pliers.
Figure 4B:
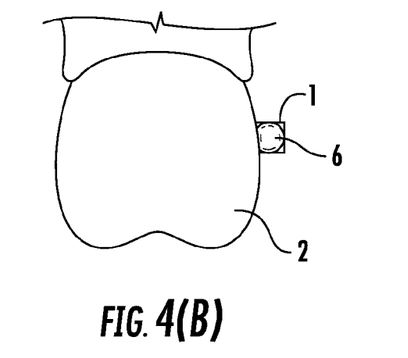
FIG. 4(b) schematically illustrates an end view of the attachment of FIG. 4(a)

Referring now to FIGS. 4(a) and 4(b) the end result of use of the safety attachment is illustrated, showing the safe-end 6 in place on the end of the wire 3. The safe-end 6 is shaped to have no sharp edges, that is to be spherical or ovoid or the like, in order to minimize the chances that it can cause any damage to the cheeks of a patient. The safety attachment can be used for all wires to apply a safe-end 6 as an anti-pull-through device and so as to ensure patients are protected from wire-pokes.

Figure 5A:
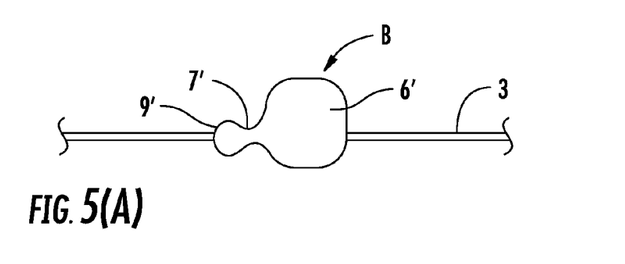
FIG. 5(a) schematically illustrates a top view of a second embodiment of a safety attachment according to the invention.
Figure 5B:
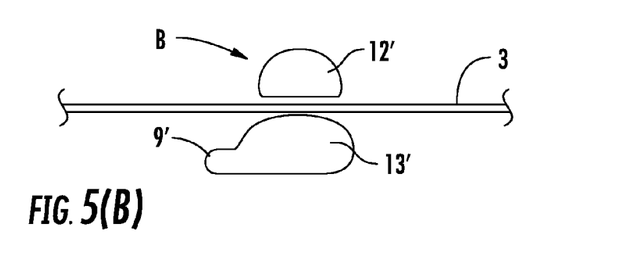
FIG. 5(b) schematically illustrates a side view of the second embodiment of the safety attachment of FIG. 5(a)

Referring now to FIGS. 5(a) and 5(b) a second embodiment of a safety attachment B according to the invention is illustrated with parts common to the first embodiment being like referenced, but with the addition of a "'". The safety attachment B is for use where there is no requirement to remove any of the wire 3, that is the wire 3 is already of the correct length, and thus no wire fragment needs to be retained and removed from the patient's mouth. Thus the safety attachment B simply comprises a safe-end 6' and a retaining lug 9' connected by an isthmus 7', these parts being substantially as previously described with reference to safety attachment A.

Figure 6A:
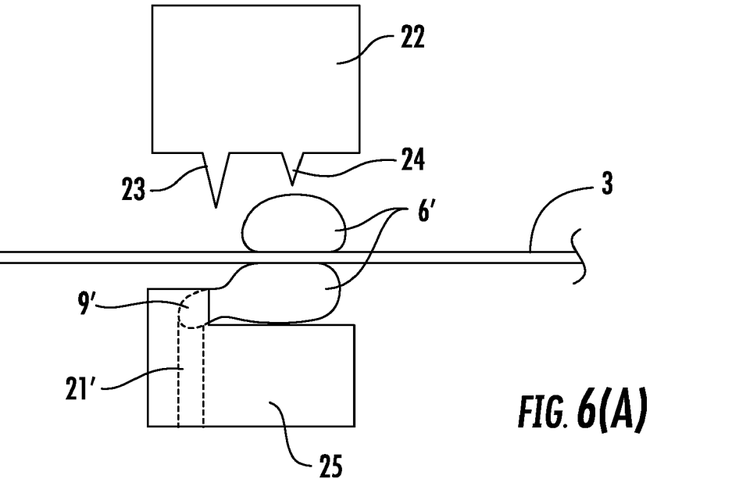
FIG. 6(a) schematically illustrates a side view of beaks of pliers used to apply the second embodiment of the safety attachment of FIG. 5(a), in side view closing around the attachment.
Figure 6B:
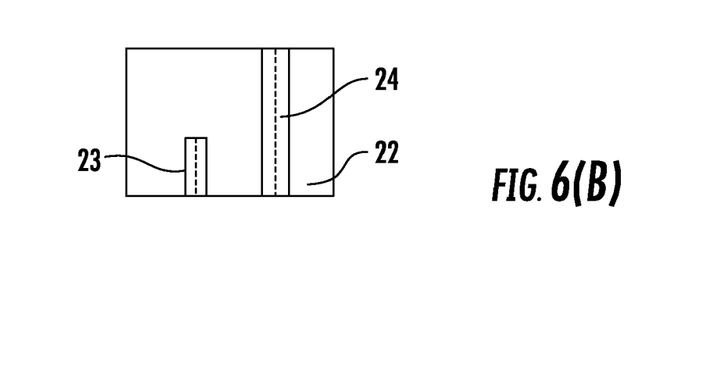
FIG. 6(b) schematically illustrates the lower face of the upper beak of the pliers of FIG. 6(a)
Figure 6C:
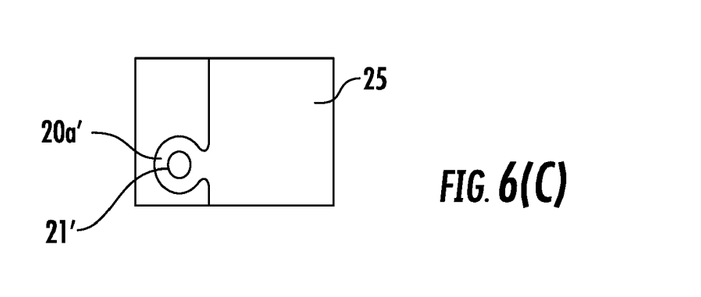
FIG. 6(c) schematically illustrates the upper face of the lower beak of the pliers of FIG. 6(a)

Referring now to FIGS. 6(a) through 6(c), upper beak 22 and lower beak 25 of pliers designed for application of the safety attachment B are illustrated schematically. The upper beak 22 carries only two blades 23 and 24. The first blade 23 is designed to cut through the isthmus T but not through the wire 3. The first blade 23 does not extend the full width of the upper beak 22, so as to avoid impinging on the wire 3. The second blade 24, which may be a multiple blade and/or which may be a flat ended broad blade, is designed to crimp the safe-end portion 6 onto the wire 3 so that it is safely retained.

As with the pliers to apply the first embodiment of the safety attachment A, there is a recess 20a' in the lower beak 25 to receive the retaining lug 9' and there is a bore 21' to accept a dental probe or similar instrument to facilitate removal of the retaining lug 9' from the pliers after use.

Figure 7A:
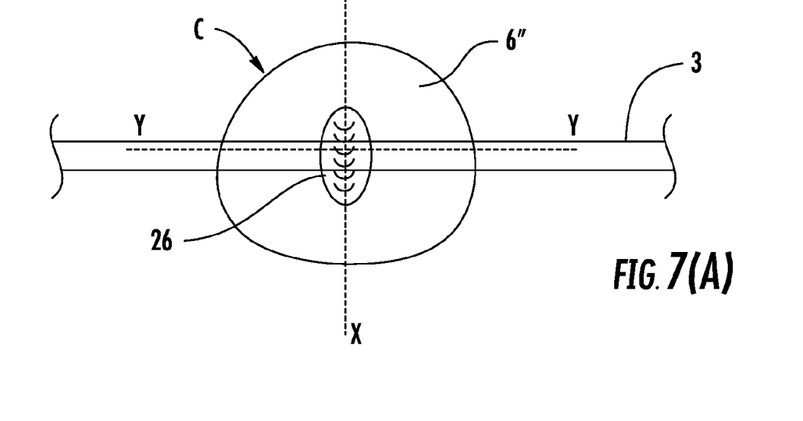
FIG. 7(a) schematically illustrates a bottom view of a third embodiment of a safety attachment according to the invention.
Figure 7B:
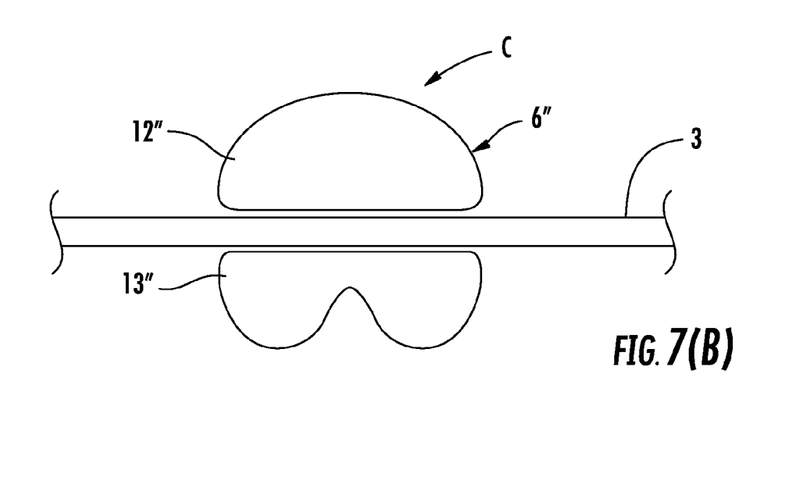
FIG. 7(b) schematically illustrates a cross section of the third embodiment of the safety attachment taken along line Y-Y of FIG. 7(a)
Figure 7C:
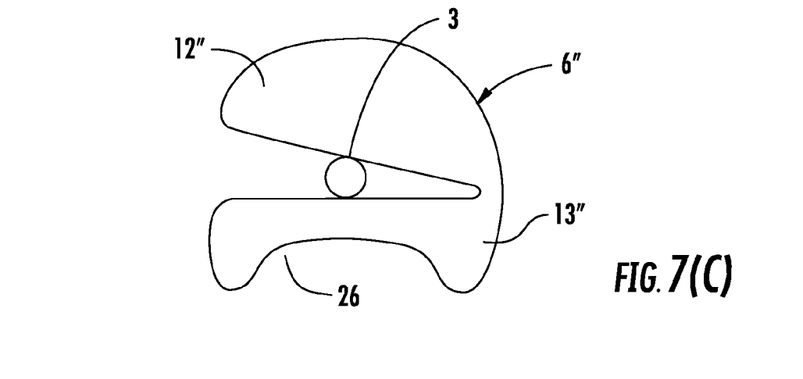
FIG. 7(c) schematically illustrates a cross section of the third embodiment of the safety attachment taken along line X-X of Figure (a)
Figure 8A:
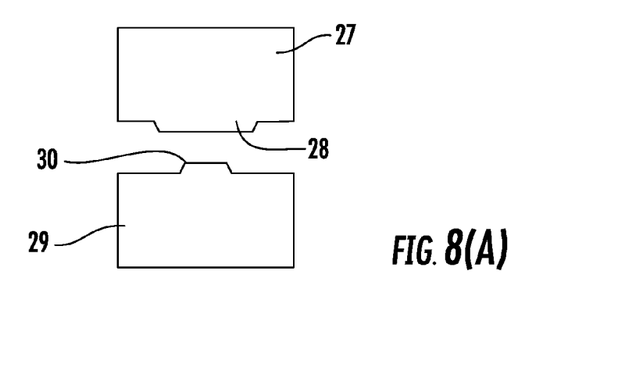
FIG. 8(a) schematically illustrates an end view of beaks of pliers used to apply the third embodiment of the safety attachment of FIGS. 7(a) through 7(c)
Figure 8B:
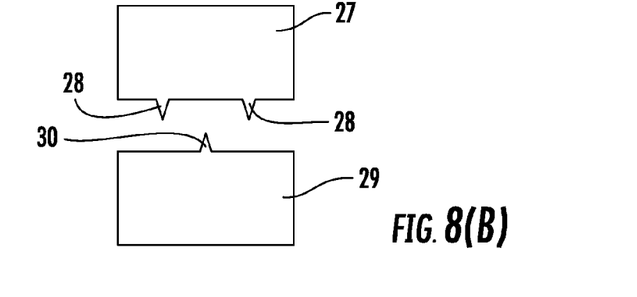
FIG. 8(b) schematically illustrates a side view of the beaks of the pliers of FIG. 8(a)
Figure 8C:
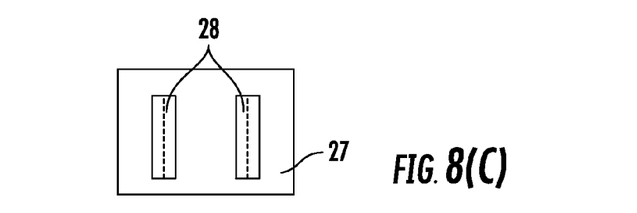
FIG. 8(c) schematically illustrates the inner face of the upper beak of the pliers of FIG. 8(a)
Figure 8D:
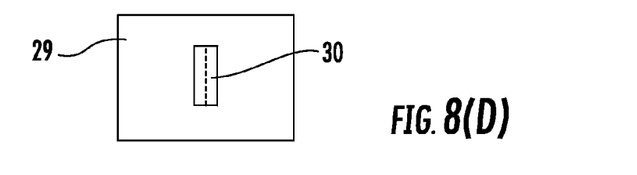
FIG. 8(d) schematically illustrates the inner face of the lower beak of the pliers of FIG. 8(a)

Referring now to FIGS. 7(a) through 7(c), a third embodiment of a safety attachment C according to the invention is shown schematically with parts common to the first embodiment being like referenced, but with the addition of a """. The safety attachment C comprises a safe-end 6", which has an indentation 26 in its lower surface.

Referring now to FIGS. 8(a) through 8(d), upper beak 27 and lower beak 29 of pliers designed for application of safety attachment C are illustrated schematically. The upper beak 27 is provided with two blades 28 designed to crimp the safe-end 6" onto the wire 3. The lower beak 29 carries a protrusion 30, running parallel to and between the blades 28 on the upper beak 27. Retention of the safety attachment C on the pliers is provided by friction between the protrusion 30 and the indentation 26, because they are an interference fit. Preferably the interference fit is only provided in direction Y-Y or direction X-X and not both directions. This is to ensure that there is sufficient freedom between the pliers and the safe-end 6" after application to the wire 3 to allow release of the pliers from the safe-end 6".

Figure 9:
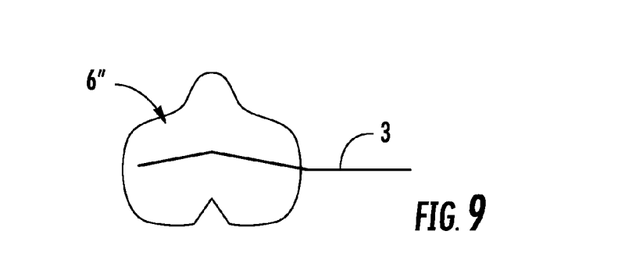
FIG. 9 schematically illustrates the third embodiment of a safety attachment according to the invention in place on a wire after application using the pliers.

Referring now to FIG. 9, the shape of the safe-end 6" after application to the wire 3 is illustrated. As can be seen the use of two blades 28 with a protrusion 30 there between has deformed both the safe-end 6" and the wire 3. This deformation of the wire 3 further assists retention of the safe-end 6" on the wire 3 and makes pull through even less likely to occur.

Figure 10A:
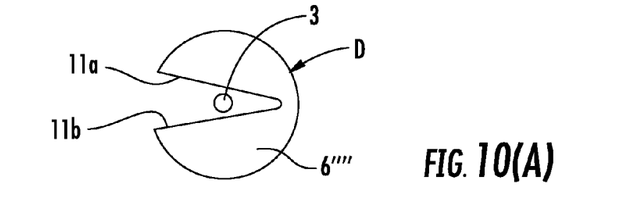
FIG. 10(a) schematically illustrates a side view of a fourth embodiment of a safety attachment according to the invention.
Figure 10B:
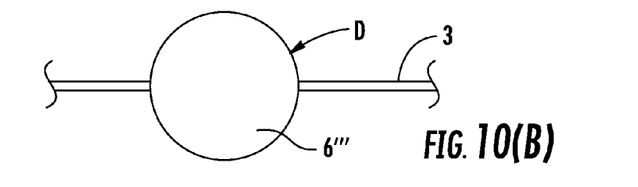
FIG. 10(b) schematically illustrates a top view of the fourth embodiment of the safety attachment of FIG. 10(a)

Referring now to FIGS. 10(a) and 10(b), a fourth embodiment of a safety attachment D according to the invention is shown schematically. The safety attachment D comprises a safe-end 6''', but being a simplified version of safety attachment C does not have an indentation in its lower surface.

Figure 11A:
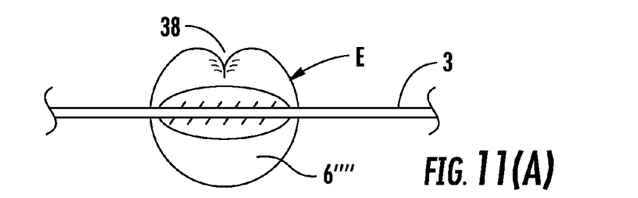
FIG. 11(a) schematically illustrates a front view of a fifth embodiment of a safety attachment.
Figure 11B:
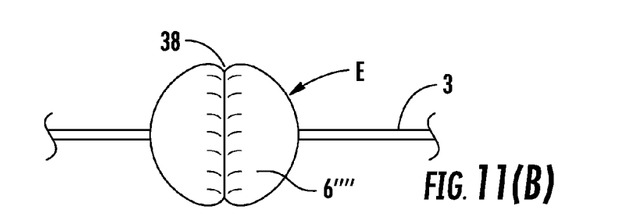
FIG. 11(b) schematically illustrates a top view of the fifth embodiment of the safety attachment of FIG. 11(a)

Referring to FIGS. 11(a) and 11(b), a fifth embodiment of a safety attachment E according to the invention is shown schematically. The safety attachment E comprises a safe-end 6'''', which has a groove 38 running along its upper surface.

Referring to FIGS. 15(a) through 15(d), a sixth embodiment of a safety attachment F according to the invention is shown schematically. The safety attachment F comprises a safe-end 6''''', which has a groove 38 running along its upper surface and a ridge 40 extending along its lower surface, the groove 38 and the ridge 40 running substantially parallel to each other and substantially perpendicular to the hinge 10 joining the upper and lower portions 12, 13. The ridge 40 is provided to assist in retaining the safety attachment F in the beaks of pliers when it is being fitted in a patient's mouth.

Figure 12A:
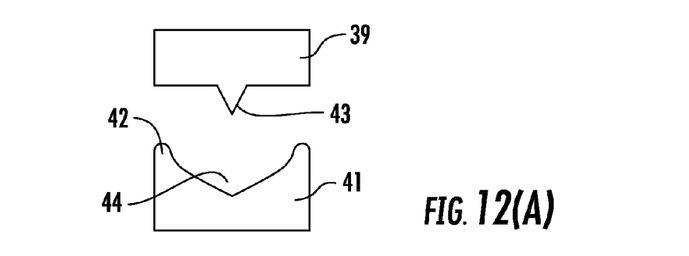
FIG. 12(a) schematically illustrates an end view of beaks of pliers for application of the fourth of fifth embodiments.
Figure 12B:
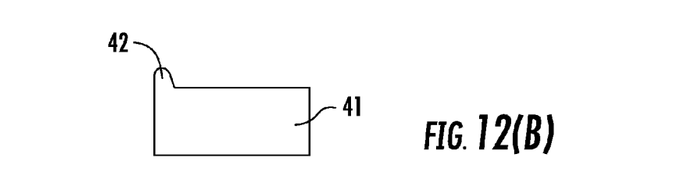
FIG. 12(b) schematically illustrates a side view of the beaks of pliers of FIG. 12(a)

Referring to FIG. 12, upper beak 39 and lower beak 41 of pliers designed for application of safety attachment D, E or F are illustrated schematically. The upper beak 39 has a blade 43 on its midline designed to crimp the safety attachment onto an orthodontic wire 3, but also to engage in the groove 38 when being used to fit safety attachment E or F. The lower beak 41 is shaped, with extensions 42 and a central recess 44, so as to accept safety attachment D, E or F and support it during insertion into the mouth, whilst also permitting deformation of the safety attachment D, E or F during crimping.

The clinical procedures for placing a safety attachment A, B, C, D, E or F are as follows.

The chosen safety attachment is inserted into the lower beak of the respective pliers, and retained as described above. The upper beak of the pliers is closed gently onto the safety attachment to further secure it. It is then possible to safely transfer the safety attachment, in the pliers, into the mouth of the patient without risk of the safety attachment being dislodged or dropped within the oral cavity even if the pliers are inverted during insertion. This permits safe use in all four corners of the mouth.

The pliers are constructed with an angle of between 80° and 145° between the beaks and the handles (not shown) so as to facilitate access to the wire protruding from the tube on the last most tooth. The safety attachment, having its hinge part 10 to the hinge of the pliers (not shown) and offering its open aspect to the outside of the pliers, is placed over the wire until the wire is hard up to the hinge part 10 of the safety attachment. The handles of the pliers are then squeezed together firmly. This action crimps the safety attachment onto the wire and, for attachments A and B also clips through the retaining lug 9 or 9' so as to allow the pliers to be removed, leaving the safe end 6, 6', 6", 6''', 6'''' or 6''''' on the wire.

Figure 13:
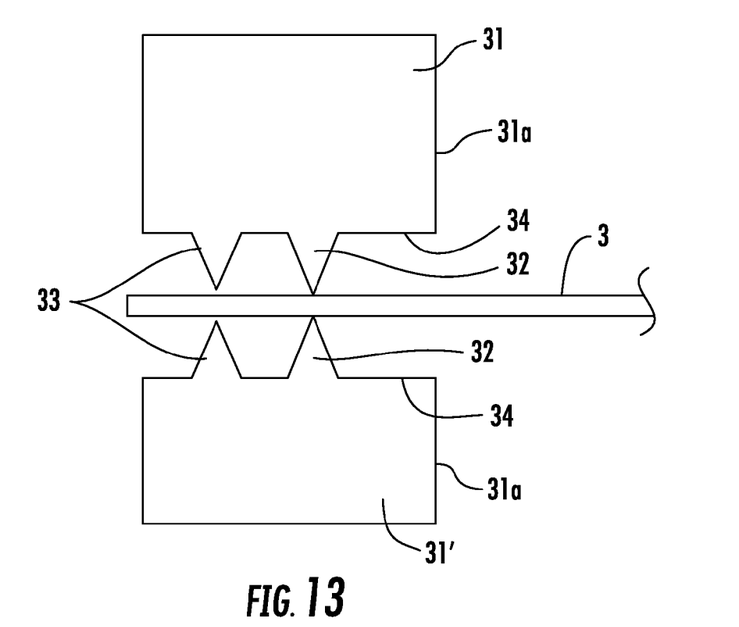
FIG. 13 schematically illustrates beaks of pliers for cutting the orthodontic wire to the length required for application of one of the safety attachments.

Referring now to FIG. 13, beaks of pliers designed to clip the protruding portion of the wire 3 to a specific length such that, when a selected safety attachment, as previously described, is applied the sharp end of the wire will be safely enclosed within the safe end thereof. The pliers have upper and lower beaks 31, 31', which each carry first blades 32 and second blades 33, which are opposed to the corresponding blades on the other beak 31, 31'. The first blades 32 are longer than the second blades 33, such that the first blades 32 sever the wire whilst the second blades 33 retain the excised fragment for safe removal from the patient's mouth. Faces 31a of the beaks 31, 31' are placed against the rear of the last most tooth during the cutting process and plain section 34 of the beaks 31, 31' acts as a spacer to ensure that the wire 3 is cut so as to leave the correct length of protruding portion behind the last most tooth.

Figure 14:
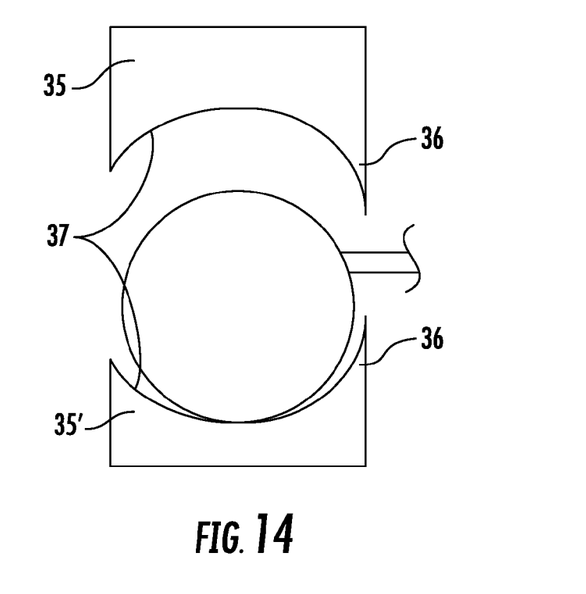
FIG. 14 schematically illustrates beaks of pliers for safe removal of one of the safety attachments, FIG. 15(a) schematically illustrates a top view of a sixth embodiment of a safety attachment according to the invention.
Figure 15A:
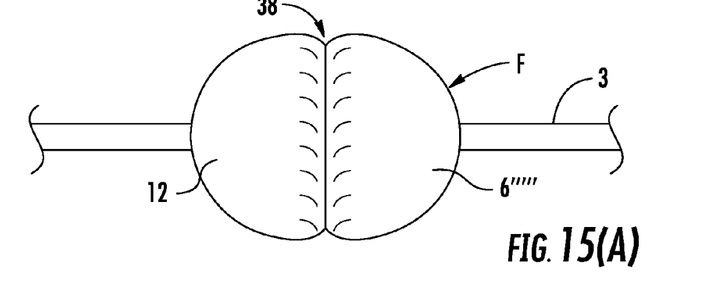
Figure 15B:
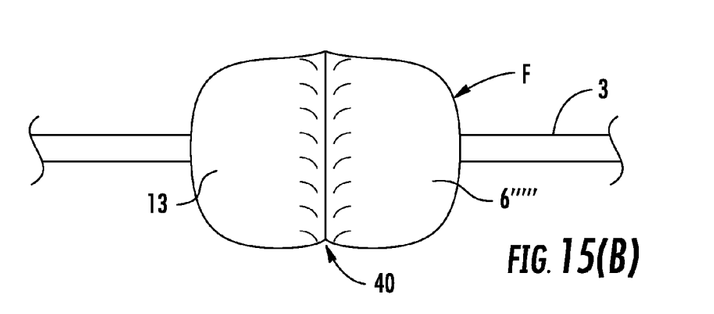
FIG. 15(b) schematically illustrates a bottom view of the sixth embodiment of the safety attachment of FIG. 15(a)
Figure 15C:
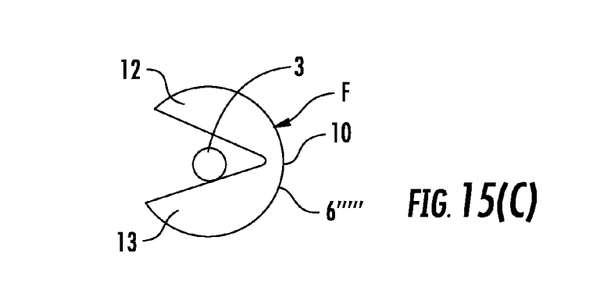
FIG. 15(c) schematically illustrates an end view of the sixth embodiment of a safety attachment of FIG. 15(a)
Figure 15D:
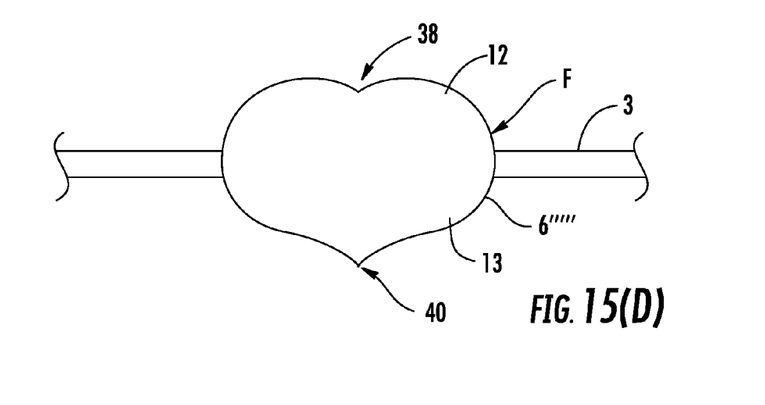
FIG. 15(d) schematically illustrates a back view of the sixth embodiment of a safety attachment of FIG. 15(a).

Referring now to FIG. 14, beaks of pliers, designed for removal of the safety attachment when it is no longer required and for its safe removal from the mouth, are illustrated. Upper and lower beaks 35, 35' each include a blade 36 for cutting the wire 3 immediately behind the last most tooth, and a recess 37 for receipt of the safe end being removed. As the blades 36 cut the wire, the remainder of each beak 35, 35' receives and grips the safe end with the previously protruding portion of the wire embedded in it, retaining it for safe removal from the patient's mouth.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The invention claimed is:

1. A combination, comprising:
   safety attachment comprising:
      a safe-end portion comprising an upper portion having a lower face, a lower portion having an upper face, and a hinge connecting the upper and lower portions to permit the lower and upper faces to be closed together, the safe-end portion having no sharp edges when lower and upper faces are closed together;
      a retaining lug extending from the lower portion, the retaining lug being positioned level with the upper face of the lower portion, and
   pliers comprising:
      an upper beak having a width and comprising at least two blades, including a cutting blade that does not extend the full width of the upper beak so as to cut through the lug only, and a crimping blade that extends the full width the upper beak.

2. The combination according to claim 1, wherein the lower and upper faces are serrated.

3. The combination according to claim 1, wherein the crimping blade is one of a plurality of crimping blades.

4. The combination according to claim 1, wherein the pliers further comprise:
   a lower beak comprising an upstand portion having a recess therein for receiving the retaining lug, the retaining lug cooperating with the recess to prevent the retaining lug from being dislodged from the recess.

5. The combination according to claim 4, wherein the lower beak of the pliers further comprises bore that extends vertically through the upstand from an outer face of the lower beak to the recess, the bore allowing insertion of an instrument to push the retaining lug out of the recess.

6. A combination, comprising:
   safety attachment comprising:
      a safe-end portion comprising an upper portion having a lower face, a lower portion having an upper face, and a hinge connecting the upper and lower portions to permit the lower and upper faces to be closed together, the safe-end portion having no sharp edges when lower and upper faces are closed together; and
      a retaining lug extending from the lower portion, the retaining lug being positioned level with the upper face of the lower portion, wherein the safety attachment further comprises:
      a wire retaining portion comprising an upper portion having a lower face, a lower portion having an upper face, and a hinge connecting the upper and lower portions to permit the lower and upper faces to be closed together independently of the lower and upper faces of the upper and lower portions of the safe-end portion, and
      an isthmus connecting the lower portion of the safe-end portion and the lower portion of the wire retaining portion, the isthmus being positioned level with the upper face of each of the lower portions.

7. The combination according to claim 6, wherein the lower and upper faces are serrated.

8. The combination according to claim 1, further comprising:
   pliers for safe removal of the safe-end portion, the pliers comprising upper and lower beaks each including a cutting blade and a recess, the recess for receiving and gripping the safe end portion as the blades cut.

9. A combination, comprising:
   a safety attachment, comprising:
      a safe-end portion comprising upper and lower portions that are connected by a hinge, a wire-retaining portion comprising upper and lower portions that are connected by a hinge, and an isthmus between the safe-end portion and the wire-retaining portion and connecting the lower portions of the safe-end portion and the wire-retaining portion; and
   first pliers comprising:
      an upper beak having three blades, comprising a first blade to crimp the upper and lower portions of the wire-retaining portion so that wire-retaining portion closes, a second blade, and a third blade to crimp the upper and lower portions of the safe-end portion so that the safe-end portion closes; and
      a lower beak, comprising a blade to fit under the connecting isthmus, the blade of the lower beak being aligned with the second blade of the upper beak, so that when the pliers are closed, the isthmus is cut to separate the wire-retaining port and the safe-end portion, the safe-end portion having no sharp edges when the isthmus is cut.

10. The combination according to claim 9, wherein
   the safety attachment further comprises:
      a retaining lug extending from the lower portion of the safe-end portion, and
   the pliers further comprises:
      an upstand portion on the lower beak, the upstand portion having a recess and an opening facing the blade of the lower beak, wherein the recess is shaped for receiving the retaining lug, the retaining lug and recess cooperating to prevent the wire retaining portion from being dislodged.

11. The combination according to claim 10, wherein the lower beak of the pliers further comprises a bore that extends vertically through the upstand from an outer face of the lower beak to the recess, the bore allowing insertion of an instrument to push the retaining lug out of the recess.

12. The combination according to claim 9, further comprising:
   second pliers comprising upper and lower beaks each including a cutting blade and a recess, the recess for receiving and gripping the safe end portion as the blades cut.

13. A combination, comprising:
   a safety attachment comprising:
      a safe-end portion comprising upper and lower portions hinged together by a hinge, the upper portion having a lower face and the lower portion having an upper face, the upper and lower portions being hinged together to permit the upper and lower faces to close together, the safe-end portion having no sharp edges when lower and upper faces are closed together, and
   first pliers comprising:
      an upper beak comprising at least two crimping blades for crimping the safe-end portion, and
      a lower beak comprising a protrusion, running parallel to and between the two blades of the upper beak, wherein the two blades and the protrusion therebetween deform the safe-end portion.

14. The combination according to claim 13, wherein the safe-end further comprises a lower surface and an indentation in the lower surface, the protrusion and the indentation being shaped and dimensioned to provide an interference fit therebetween, whereby the safe-end portion is retained on the pliers by friction between the protrusion and the indentation.

15. The combination according to claim 14, wherein the interference fit is only provided in one direction.

16. The combination according to claim 13, further comprising:
    second pliers comprising upper and lower beaks each including a cutting blade and a recess, the recess for receiving and gripping the safe end portion as the blades cut.

17. A combination, comprising:
    a safety attachment comprising:
        a safe-end portion comprising upper and lower portions hinged together by a hinge, wherein the upper portion has a lower face and the lower portion has an upper face, the upper and lower portions being hinged together to permit the upper and lower faces to close together, the safe-end portion having no sharp edges when lower and upper faces are closed together, and
    first pliers comprising:
        an upper beak comprising a central crimp blade, and
        a lower beak shaped with extensions and a central recess between the extensions to accept the safe-end portion and support the safe-end portion while permitting deformation of the safe-end portion when crimping the safe-end portion.

18. The combination according to claim 17, wherein the safe-end portion further comprises an upper surface and a groove extending along the upper surface, the central crimp blade of the upper beak engaging the groove.

19. The combination according to claim 18, wherein the safe-end portion further comprises a lower surface and a ridge extending along the lower surface, wherein the groove and the ridge run substantially parallel to each other and substantially perpendicular to the hinge joining the upper and lower portions, the ridge assisting in retaining the safe-end portion in the beaks of pliers.

20. The combination according to claim 17, further comprising:
    second pliers comprising upper and lower beaks each including a cutting blade and a recess, the recess for receiving and gripping the safe end portion as the blades cut.

* * * * *